United States Patent [19]
Gurol et al.

[11] Patent Number: 6,066,342
[45] Date of Patent: *May 23, 2000

[54] ANTACID COMPOSITION

[75] Inventors: Ismail Macit Gurol, Seattle, Wash.; Kyle William Gano, Los Angeles, Calif.

[73] Assignee: Tamer International, Ltd., Seattle, Wash.

[ * ] Notice: This patent issued on a continued prosecution application filed under 37 CFR 1.53(d), and is subject to the twenty year patent term provisions of 35 U.S.C. 154(a)(2).

[21] Appl. No.: 08/772,168

[22] Filed: Dec. 20, 1996

Related U.S. Application Data

[63] Continuation-in-part of application No. 08/577,147, Dec. 22, 1995, Pat. No. 5,853,787.

[51] Int. Cl.[7] ................................................. A01N 59/06
[52] U.S. Cl. ......................... 424/687; 424/688; 424/689; 424/692
[58] Field of Search ................................... 424/687, 688, 424/689, 692

[56] References Cited

U.S. PATENT DOCUMENTS

| | | |
|---|---|---|
| 243,521 | 6/1881 | Davidson . |
| 312,516 | 2/1885 | Schilling . |
| 680,889 | 8/1901 | Schutz . |
| 1,137,265 | 4/1915 | Hübner . |
| 1,742,261 | 1/1930 | Klein . |
| 1,822,227 | 9/1931 | Lendrich et al. . |
| 2,036,345 | 4/1936 | Merkel . |
| 2,419,031 | 4/1947 | Pollack . |
| 2,477,080 | 7/1949 | Necheles et al. . |
| 2,518,441 | 8/1950 | Schaeppi et al. . |
| 2,626,558 | 1/1953 | Stein . |
| 2,687,355 | 8/1954 | Benner et al. . |
| 2,889,226 | 6/1959 | Hinkley . |
| 3,644,122 | 2/1972 | Yeransian . |
| 4,104,370 | 8/1978 | Bloch . |
| 4,327,076 | 4/1982 | Puglia et al. ............................. 424/38 |
| 4,461,778 | 7/1984 | Vialatte née Geolier . |
| 4,514,389 | 4/1985 | Miyata . |
| 4,576,819 | 3/1986 | Miyata et al. . |
| 4,755,385 | 7/1988 | Etienne et al. ........................... 424/154 |
| 4,801,608 | 1/1989 | Bos et al. . |
| 4,857,332 | 8/1989 | Schricker . |
| 4,904,473 | 2/1990 | Schricker et al. . |
| 4,976,963 | 12/1990 | Schricker et al. . |
| 4,976,983 | 12/1990 | Hirsh et al. . |
| 4,980,175 | 12/1990 | Chavkin et al. ......................... 424/677 |
| 4,985,271 | 1/1991 | Neilson et al. . |
| 5,068,109 | 11/1991 | Foldager et al. ........................ 424/441 |
| 5,147,666 | 9/1992 | Doonan et al. . |
| 5,229,155 | 7/1993 | Weisemann et al. . |
| 5,306,511 | 4/1994 | Whang . |
| 5,314,852 | 5/1994 | Klatte . |
| 5,350,591 | 9/1994 | Canton . |
| 5,461,082 | 10/1995 | Machimura et al. . |
| 5,498,426 | 3/1996 | Wilson et al. . |

OTHER PUBLICATIONS

Barrett–Connor, E., et al., "Coffee–Associated Osteoporosis Offset by Daily Milk Consumption," *Journal of the American Medical Association,* Jan. 26, 1994, vol. 271, No. 4, pp. 280–283.

"Ground Coffee," *Consumer Reports,* Jan. 1991, pp. 30–50.

Hornstein, I., "Flavor Chemistry," symposium, American Chemical Society, Detroit, MI, 1966, pp. 180–187.

Peterson, M.S., et al., *Encyclopedia of Food Science,* 1978, pp. 1–6.

Pintauro, N., "Soluble Coffee Manufacturing Processes," Noyes Development Corp., 1969, pp. 72–73, 116–129.

Ukers, W., *Tea and Coffee Trade Journal,* 1935, pp. 292–296.

*Primary Examiner*—Dwayne C. Jones
*Attorney, Agent, or Firm*—Christensen O'Connor Johnson & Kindness pllc

[57] ABSTRACT

An antacid composition containing 20 to 75 weight percent calcium carbonate, 0.1 to 10 weight percent magnesium hydroxide, and 0.5 to 10 weight percent potassium hydroxide is disclosed. A method for neutralizing excess stomach acid by oral administration of the antacid composition of the invention is also disclosed.

8 Claims, 2 Drawing Sheets

ANTACID COMPOSITION

CROSS-REFERENCE TO RELATED APPLICATION

This application is a continuation-in-part of U.S. patent application Ser. No. 08/577,147, filed Dec. 22, 1995, now U.S. Pat. No. 5,853,787, priority of the filing date of which is hereby claimed under 35 U.S.C. § 120.

FIELD OF THE INVENTION

The present invention relates generally to an antacid composition for neutralizing excess stomach acid, and more specifically to an antacid composition that includes potassium hydroxide.

BACKGROUND OF THE INVENTION

The oral administration or consumption of acid neutralizing agents (antacids) to treat excess gastric acid and relieve its associated discomfort is well known. Generally, antacid compositions include, as active ingredients, one or more alkaline substances in combination with other inactive ingredients. The antacid composition's alkaline components effect gastric acid neutralization while the inactive ingredients serve either as a carrier to facilitate administration or to enhance the composition's appeal, palatability, dispensability, and ease of manufacture.

Ideally, an antacid provides rapid and long-lasting relief from the discomfort associated with excess stomach acid. In addition, an effective antacid provides rapid and long-lasting relief in a convenient administrable form and dosage.

A variety of alkaline substances have been previously employed as active ingredients in antacid formulations. For example, U.S. Pat. No. 4,801,608 to Bos et al. describes a bismuth containing composition that is effective for the treatment of peptic ulcers. Aluminum hydroxide containing antacid compositions have been described in U.S. Pat. Nos. 4,514,389 and 4,576,819 to Miyata et al. and U.S. Pat. No. 5,461,082 to Machimura et al. Carbonates and bicarbonates of sodium, potassium, and calcium have also been employed as acid neutralizing agents in various antacid formulations. See, for example, U.S. Pat. No. 4,327,076 to Puglia et al. (calcium carbonate); U.S. Pat. Nos. 4,857,332; 4,904,473, and 4,976,963 to Schricker et al. (calcium carbonate and sodium bicarbonate); and U.S. Pat. No. 5,498,426 to Wilson et al. (calcium carbonate and potassium bicarbonate).

Acid neutralizing agents have also been combined with various carriers in the formulation of antacid compositions. For example, U.S. Pat. No. 2,477,080 to Necheles et al. relates to an antacid preparation composed of an acid neutralizing agent such as magnesium oxide, calcium carbonate, or sodium bicarbonate, and a carrier, carboxymethyl cellulose, to increase the residency time of the acid neutralizing agent in the stomach and thereby afford long-lasting antacid activity.

Although the active ingredients of commercially available, over-the-counter antacid compositions vary, many of these antacids include alkaline earth (e.g., calcium and magnesium) carbonates and hydroxides. More specifically, calcium carbonate is a primary acid neutralizing agent common to many commercially available antacid formulations (e.g., ROLAIDS, TUMS, MYLANTA, MEDACID). In fact, calcium carbonate is the sole active ingredient in TUMS. To counteract its constipative effect, calcium carbonate is often used in combination with magnesium salts such as magnesium carbonate, magnesium hydroxide, and magnesium oxide, in antacid compositions (e.g., ROLAIDS, MYLANTA, MEDACID).

Generally, antacid compositions containing weak acid neutralizing agents such as calcium carbonate and aluminum hydroxide are slow acting and consequently do not provide rapid relief to the discomfort associated with excess stomach acid. More rapid acting antacids may include magnesium hydroxide, a stronger acid neutralizing agent. Although primarily incorporated into calcium carbonate containing antacids for its anticonstipative effect, magnesium hydroxide is also known for its antacid activity.

Other more highly alkaline substances, such as sodium and potassium hydroxide, exhibit a still stronger neutralizing effect. However, despite their great ability to neutralize acid, the sodium and potassium hydroxide have not been used as active ingredients in antacid compositions for human consumption. This is apparently due to the corrosive nature of these strong bases. Potassium hydroxide, for example, can be extremely corrosive to all tissues, and ingestion of significant quantities in some circumstances can produce pain in the throat and epigastrium, hematemesis, collapse, and stricture of the esophagus. In extreme cases, ingestion may be fatal. Sodium hydroxide is similarly caustic and toxic.

Although not specifically incorporated as an active antacid ingredient, potassium hydroxide is included among the ingredients as a potassium source in a ruminant feed composition described in U.S. Pat. No. 4,976,963 to Schricker et al. and in the colloidal antacid described in U.S. Pat. No. 4,801,608 to Bos et al. Schricker's feed pellet includes an antacid component (i.e., a mixture of a sodium or magnesium antacid) and an electrolyte component to provide potassium, sodium, and chlorine (i.e., a potassium, sodium, or chlorine-containing electrolyte) in the diet. Potassium hydroxide is described in the patent as a suitable potassium source. The colloidal bismuth antacid composition of Bos optionally includes potassium hydroxide to maintain the pH of the colloidal suspension in a range so as prevent the precipitation of bismuth from the colloid.

In at least one instance, potassium hydroxide has been utilized as an acid neutralizing agent in a feed additive for nonhuman consumption. U.S. Pat. No. 5,314,852 to Klatte describes a potassium hydroxide-impregnated zeolite that is useful as a feed supplement to ruminant animals (e.g., cows) to provide buffering in several digestive organs. However, Klatte cautions that the activity rate may be too high for some animal feed applications and that potassium hydroxide is much too caustic to feed alone to such animals.

Accordingly, despite the great number of antacid compositions, some of which are noted above, there remains a need for a rapid acting and long-lasting antacid composition that may be orally administered in a safe and effective amount to an individual suffering from the discomfort associated with excess stomach acid. The present invention seeks to fulfill these needs and provides further related advantages.

The consumption of acidic food and beverages often results in physical discomfort in the form of indigestion and heartburn, among other discomforts. Acidic beverages including coffees and teas are particularly troublesome because of their widespread consumption and elevated acid concentrations.

Coffee is a morning ritual for over 125 million Americans, with the average coffee drinker consuming three cups of coffee per day. However, drinking coffee does not affect all people in the same way. While some are able to drink an entire pot of coffee without experiencing any adverse effects, others may experience indigestion and discomfort. In addition to discomfort, potential health risks associated with excessive coffee consumption in general, and with caffeine consumption in particular, have been theorized. At least one study has linked coffee consumption to osteoporosis. Pregnant mothers are often cautioned to limit their intake of coffee as a precaution to ensure the health and safety of their unborn children. It is not well understood what the effects of coffee acids may be on the health of the general population, but at a minimum acidic coffee causes discomfort for many people with digestive tract disorders, such as acid reflux or ulcers.

Coffee is a complex composition derived from the brewing of roasted and ground coffee beans. The constituents of coffee beans include caffeine (1–2%), coffee oil (10–15%), sucrose and other sugars (about 8%), proteins (about 11%), ash (about 5%), and chlorogenic and caffeic acids (about 6%). Other constituents include cellulose, hemicelluloses, trigonelline, carbohydrates, volatile oils, and other acids. The composition of a particular coffee is variable and depends upon such factors as the type of bean, where the coffee is grown and harvested, and how the beans are processed. It is the individual constituents of a coffee that contribute to its natural aroma, flavor, and appeal.

Many different acidic constituents are present in coffee. Coffee's acids include malic acid, tannic acid, maleic acid, oleic acid, oxalic acid, caffeic acid, and chlorogenic acid, among others. These acidic constituents are responsible for the overall acidity of coffee and the discomfort that occasionally arises from the ingestion of this acidic beverage. Furthermore, coffee contains caffeine, which, upon ingestion, causes the gastric secretion of acids. Accordingly, coffee drinking not only results in the ingestion of an acidic beverage, but also stimulates the production of additional acids.

Commonly, the coffee drinker's solution to discomfort arising from coffee's acidity is to either reduce the number of cups of coffee consumed each day, avoid drinking coffee entirely, or alternatively, dilute the coffee, or accompany coffee drinking, with dairy products such as milk or cream. Unfortunately, the use of dairy products as a solution to the problem of coffee acidity is not universal. Many people, including some coffee drinkers, suffer from lactose intolerance and have difficulty in digesting milk sugars. For these individuals, the problem of coffee acidity is not solved by the addition of milk products to coffee.

The problem of reducing the acidity of certain foods and beverages has been previously addressed. For example, a process for decreasing the malic acid content in wines involving the treatment of wine with a composition including calcium carbonate, potassium bicarbonate, and calcium tartrate has been described. U.S. Pat. No. 4,461,778. A malolactic fermentation process that provides a coffee product having reduced malic acid content has also been described. U.S. Pat. Nos. 4,976,983 and 5,147,666. A common practice in red wine production involves treating the wine with gelatin, which selectively neutralizes tannic acid.

Alkaline treatments have been used in the production of coffee products. For example, in the preparation of instant coffee, coffee extracts have been treated with alkaline materials including ammonia, alkali metal and alkaline earth metal hydroxides, carbonates, and bicarbonates to improve the yield of soluble solids. U.S. Pat. No. 3,644,122. Similarly, alkaline molecular sieves have been employed in a process for improving yield in secondary coffee extracts in the production of soluble coffee. U.S. Pat. No. 5,229,155. A process for preparing a better tasting coffee involving an intermediate step of treating partially roasted coffee beans with an aqueous alkaline solution of a foodgrade base, such as sodium hydroxide, ammonium hydroxide, calcium hydroxide, or ammonium bicarbonate, prior to final roasting is also known. U.S. Pat. No. 4,986,271.

In some cultures, roasted and ground coffee is customarily brewed together with egg and eggshells. Presumably, this treatment reduces the acidity of the resulting brewed coffee. W. Ukers, *Tea and Coffee Trade Journal*, 1935. To bring out the full flavor and strength of coffee, a coffee composition comprising a roasted coffee bean coated with alkali, such as borax or bicarbonate of soda, has been disclosed. U.S. Pat. No. 312,516. Today, borax is considered unsafe for human consumption, and the ingestion of sodium is often considered inadvisable for individuals on low sodium diets. An alkaline substance, lithium carbonate, has been utilized as a preserving agent for roasted and ground coffee. U.S. Pat. No. 2,419,031. A process for making coffee more digestible by raising its pH by the addition of an acid binding substance is also known. U.S. Pat. No. 2,036,345. In this process, the acid binding substance is a basic or alkaline material non-injurious to health and includes alkaline earth metal oxides, hydroxides, carbonates, and bicarbonates as well as alkali metal carbonates, bicarbonates, and alkaline phosphates. In a preferred embodiment, the acid binding substance includes trisodium phosphate and potassium bromide. Today, neither of these two ingredients is considered by the Food and Drug Administration to be Generally Regarded As Safe (GRAS).

Accordingly, despite the methods and compositions for treating coffee mentioned above, there remains a need in the art for a composition and method for reducing the acidity of foods and beverages, such as coffee, that are safe for a broad segment of the population, economical, and easy to use. The present invention addresses these needs and provides further related advantages.

SUMMARY OF THE INVENTION

The present invention relates generally to antacid and acid-neutralizing compositions and methods of their use in neutralizing acids. In one aspect of the present invention, an antacid composition that is useful in neutralizing excess stomach acid and relieving discomfort in persons suffering from acid indigestion is disclosed. In another aspect, the present invention discloses an acid-neutralizing composition that is useful in reducing the acidity of acidic foods and beverages.

In one aspect, the invention relates to an antacid composition comprising an alkaline earth metal carbonate, preferably calcium carbonate; an alkali metal hydroxide, preferably potassium hydroxide; and an alkaline earth metal hydroxide, preferably magnesium hydroxide. In a preferred embodiment, calcium carbonate is present in the composition in an amount ranging from 20 to 90 percent by weight of the total composition, potassium hydroxide is present in an amount ranging from 0.5 to 5 percent by weight of the total composition, and magnesium hydroxide is present in an amount ranging from 0.1 to 10 percent by weight of the total composition. The antacid formulation may additionally include potassium chloride, an excipient, and a flavoring agent. Suitable excipients include granulating agents such as microcrystalline cellulose, croscarmellose sodium NF, and silicon dioxide. Suitable flavoring agents include spearmint flavorant, sucrose, fructose, and NutraSweet®. In a particularly preferred embodiment, the antacid composition includes calcium carbonate, potassium hydroxide, magnesium hydroxide, microcrystalline cellulose, croscarmellose sodium NF, silicon dioxide, a spearmint flavorant, and sucrose.

In another aspect, the present invention discloses a method for neutralizing excess stomach acids. In the method, a safe and effective amount of an antacid composition including calcium carbonate, potassium hydroxide, and magnesium hydroxide is orally administered to a human in need thereof.

The present invention additionally relates to methods of reducing the acidity of acidic foods and acidic beverages through the use of an acid-neutralizing composition. More specifically, the present invention relates to methods and compositions for brewing coffee having reduced acidity. The availability of methods and compositions of this invention to the general public enables the consumer, for the first time, to adjust the acidity of any food or beverage to suit the consumer's taste. Previous methods were available only to manufacturers.

In an aspect of the invention, methods of brewing coffee having reduced acidity are disclosed. In the method, an acid-neutralizing composition is added to a coffee product in an amount sufficient to produce a brewed coffee having a pH of from about 5.7 to about 6.1. In an embodiment, the method includes adding an acid-neutralizing composition to whole coffee beans. In another embodiment, the method includes the addition of an acid-neutralizing composition to ground coffee beans. In yet another embodiment, the method includes the addition of an acid-neutralizing composition to a brewed coffee beverage. In still another embodiment, the method includes brewing coffee utilizing a coffee filter impregnated with an acid-neutralizing composition.

In another aspect, the present invention discloses an acid-neutralizing composition. In general, the acid-neutralizing composition comprises alkaline (i.e., basic) substances and affords both rapid and long-lasting antacid activity. Suitable alkaline substances of the present invention include alkaline earth metal carbonates, alkali and alkaline earth metal hydroxides, and aluminum hydroxide. In a preferred embodiment, the alkaline substances include calcium carbonate, potassium hydroxide, and magnesium hydroxide. The acid-neutralizing composition may additionally include potassium chloride, gelatin, bacteria and fungi retarders, vitamin D, and excipients. Suitable excipients include granulating agents, dispersing agents, instant coffee, and nondairy creamers. In a particularly preferred embodiment, the acid-neutralizing composition includes calcium carbonate, potassium hydroxide, magnesium hydroxide, potassium chloride, vitamin D, and instant coffee.

In another embodiment, the present invention includes a coffee product comprised of whole coffee beans and an acid-neutralizing composition. In a further embodiment, the invention includes a coffee product comprised of ground coffee beans and an acid-neutralizing composition.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
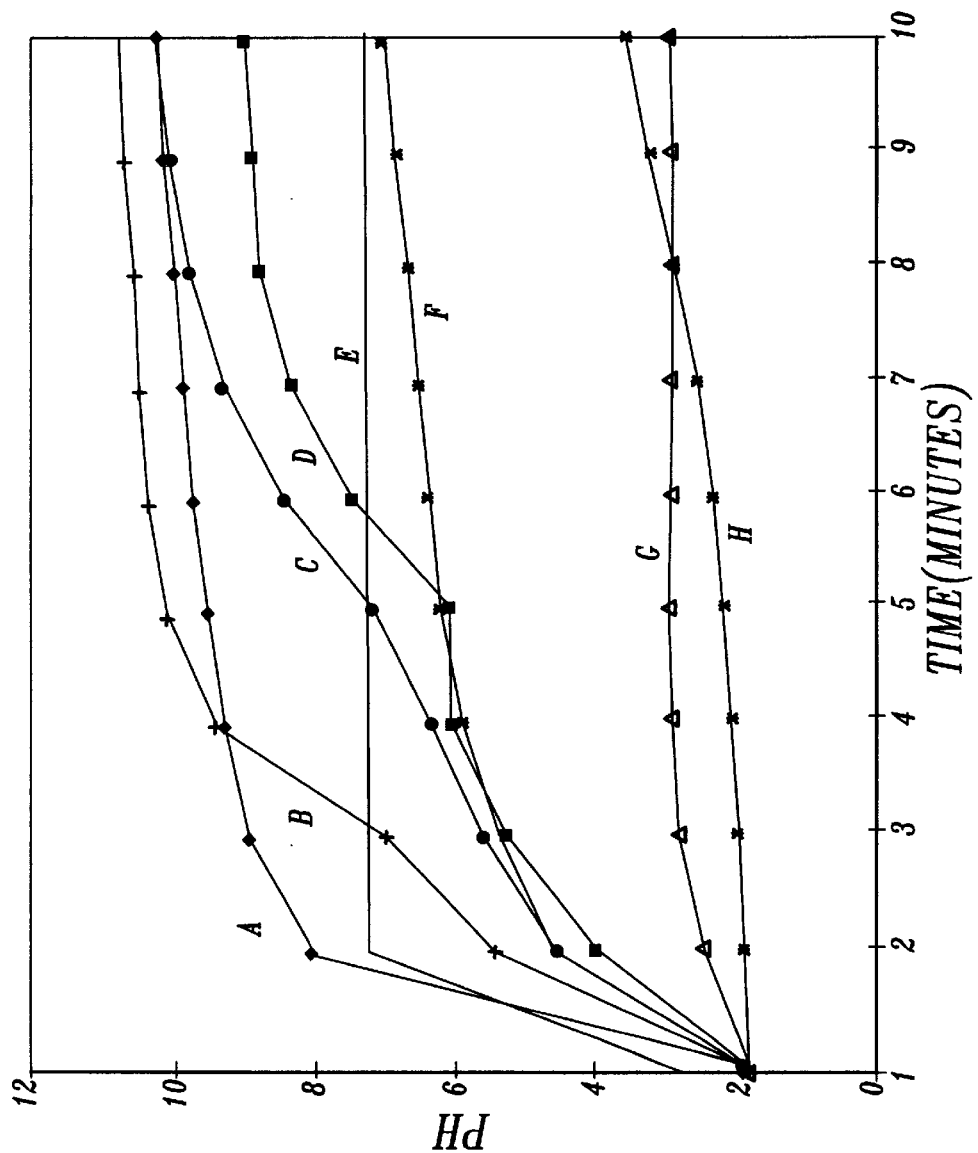
FIG. 1 is a graph comparing the change in pH over time of acidic solutions treated with a representative antacid composition of the present invention (a) and several commercially available antacids: MEDACID (b), ROLAIDS (c), MYLANTA (d), PRELIEF (e), TUMS (f), GAVISCON (g), and MAALOX (h)

The present invention relates generally to antacid and acid-neutralizing compositions and methods for their use in neutralizing acid. As used herein, the terms "antacid" and "acid-neutralizing" are used interchangeably and refer to compositions that, when added to an acidic environment, reduce the acidity of the environment. In one aspect, the present invention generally relates to methods and compositions useful in reducing the acidity of acidic foods and beverages. In this aspect, the present invention is directed to methods and compositions for brewing coffee having reduced acidity. In another aspect, the invention relates generally to methods and compositions useful in neutralizing excess stomach acid and relieving discomfort in humans suffering from acid indigestion.

In one aspect of the invention, methods of brewing coffee having reduced acidity is disclosed. In these methods, the acidity of coffee is reduced through the use of an acid-neutralizing composition. The methods of the present invention provide a brewed coffee having a pH of from about 5.7 to about 6.1. The methods are applicable to brewing methods that utilize either whole or ground coffee beans. The present invention also includes a method for reducing the acidity of a brewed coffee beverage. As noted above, the methods are also applicable to reducing the acidity of liquid foods.

In another aspect of the present invention, an acid-neutralizing composition is disclosed. The acid-neutralizing composition comprises alkaline (i.e., basic) substances and affords both rapid and long-lasting antacid activity. As used herein, the term "antacid activity" refers to the ability of a substance to neutralize and/or to buffer an acid. Neutralization refers to a acid-base reaction by which an acid is made neutral. Neutralization does not necessarily mean attaining neutral pH (i.e., pH 7), rather, neutralization refers to the equivalence point for a particular acid-base reaction and will depend upon the respective strengths of the particular acid and base, their relative concentrations, and the buffering properties of the solution containing the acid and base. A buffer is a solution containing salts of weak acids that is capable of neutralizing both acids and bases and acts to maintain the pH of a solution. In other words, a buffered solution contains both a weak acid (e.g., acetic acid) and its conjugate weak base (e.g., sodium acetate) and its pH changes only slightly upon the addition of acid or base. The weak acid acts as a buffer when base is added to the solution, and the weak base acts as a buffer when acid is added to the solution. In the context of the present invention, the addition of an acid-neutralizing composition to an acidic food or beverage results in the neutralization of acids, thereby reducing the acidity of the food or beverage. At the same time, the food or beverage becomes buffered, that is, the pH of the food or beverage may be maintained, within limits, upon the addition of more acid.

Alkaline substances having long-lasting antacid activity include alkali and alkaline earth metal carbonates. For example, the pharmaceutical use of calcium carbonate as an effective stomach antacid is well known. The rapid antacid effect of stronger alkaline substances such as alkali and alkaline earth metal hydroxides is also known. Commonly used alkali and alkaline earth metal hydroxides include lithium, sodium, potassium, calcium, and magnesium hydroxides.

As noted above, the acid-neutralizing composition of this invention includes a combination of alkaline substances having both rapid and long-lasting antacid activity. As such, the composition of the present invention is particularly well suited for reducing the acidity of caffeinated beverages such as coffee. The rapid acting alkaline substances (e.g., potassium hydroxide and magnesium hydroxide) of the composition effectively reduce the acidity of the beverage itself, while the long-lasting alkaline substances (e.g., calcium carbonate) counteract and neutralize acidic gastric secretions stimulated by the ingestion of caffeine.

The alkaline substances of the present invention include alkaline earth metal carbonates, alkali and alkaline earth metal hydroxides, and aluminum hydroxide. More specifically, alkaline earth metal carbonates include calcium and magnesium carbonates, and alkali and alkaline earth metal hydroxides include potassium and magnesium hydroxides. In addition to alkaline substances, the acid-neutralizing composition includes potassium chloride. In a preferred embodiment, the acid-neutralizing composition comprises calcium carbonate, potassium hydroxide, magnesium hydroxide, and potassium chloride. In suitable embodiments, calcium carbonate is present in the composition in an amount ranging from about 60% to about 90% by weight of the total composition, potassium hydroxide is present in an amount ranging from about 5% to about 15% by weight of the total composition; magnesium hydroxide is present in an amount ranging from about 0.1% to about 10% by weight of the total composition; and potassium chloride is present in an amount ranging from about 1% to about 5% by weight of the total composition.

In a preferred embodiment, calcium carbonate is present in the composition in an amount ranging from about 65% to about 80% by weight of the total composition; potassium hydroxide is present in an amount ranging from about 6% to about 8% by weight of the total composition, magnesium hydroxide is present in an amount ranging from about 0.5% to about 2% by weight of the total composition; and potassium chloride is present in an amount ranging from about 2% to about 3% by weight of the total composition.

Of these acid neutralizing compounds, potassium hydroxide is the most active neutralizer, effective at neutralizing maleic, oxalic, and to some extent, chlorogenic acids. The remaining compounds of the preferred composition are less active. Magnesium hydroxide supplements the neutralizing effect of the potassium hydroxide, and is the secondmost active neutralizer. Calcium carbonate acts as a weak neutralizer, but also serves as a diluent to provide a convenient application quantity of the composition, and as a calcium source. The potassium chloride is included primarily for flavor, providing a salty flavor to substitute for the acid flavor of untreated coffee. The combination of these ingredients of the composition provides a highly effective acid neutralizer that does not detrimentally alter the flavor of treated brewed coffee.

The alkaline substances noted above are the active ingredients primarily responsible in reducing the acidity of an acidic food or beverage. In addition to their antacid activity, the alkaline substances provide additional effects beneficial to health and nutrition. For example, magnesium hydroxide present in the composition has the effect of counteracting the constipative effect that often accompanies the ingestion of calcium carbonate. Furthermore, from a dietary standpoint, the alkaline substances also provide calcium, potassium, and magnesium, minerals for which the Food and Drug Administration has proposed minimum daily requirements.

In another embodiment of the acid-neutralizing composition, in addition to the alkaline substances noted above, the composition further includes foodgrade gelatin as an active ingredient. In a preferred embodiment, the gelatin is foodgrade, type B gelatin. Generally, for the acid-neutralizing compositions of the invention that include gelatin, gelatin is present in an amount up to about 3% by weight of the total composition. The gelatin is useful in the composition for neutralizing tannic acid, an acid present in the fruit of many plants, and one of the acids present in coffee. In a preferred embodiment, acid-neutralizing compositions that include gelatin also include a bacteria and/or fungi retarder. Suitable bacteria and/or fungi retarders include any such retarder that is effective in preventing the growth of bacteria and/or fungi in the composition. The bacteria and/or fungi retarder is present in an amount to effectively prevent the growth of bacteria and/or fungi, typically in an amount ranging from about 0.01% to about 0.2% by weight of the total composition. Preferred bacteria and/or fungi retarders include methyl paraben and propyl paraben. In one preferred embodiment, the acid-neutralizing composition includes methyl paraben in an amount ranging from about 0.01% to about 0.03% by weight of the total composition and propyl paraben in an amount ranging from about 0.07% to about 0.09% by weight of the total composition.

In addition to the alkaline substances mentioned above, the acid-neutralizing composition of this invention may include other ingredients. Thus, in another embodiment, the acid-neutralizing composition includes vitamin D. Preferably, vitamin D is vitamin $D_3$ and is present in the composition in an amount ranging from about 0.1% to about 0.5% by weight of the total composition. Addition of an amount of the acid-neutralizing composition sufficient to produce a cup of coffee having a pH of from about 5.7 to about 6.1 provides a cup of coffee having about 100 IU (international units) of vitamin D. While vitamin D is not an alkaline substance useful in reducing acidity, vitamin D is active in calcium uptake. Accordingly, because of the beneficial aspects of dietary calcium (i.e., recommended daily allowance of 800 to 1500 milligrams) and because the composition of this invention includes calcium as a primary ingredient, the addition of vitamin D to the composition provides further nutritional and health benefits.

The composition of this invention may also include an excipient. As used herein, the term "excipient" refers to an inert substance that forms a vehicle for the active ingredients of the composition. In the context of the present invention, suitable excipients include those that permit the effective and efficient delivery of the alkaline substances and other ingredients present in the composition of this invention, and include granulating and dispersing agents. For example, the acid-neutralizing composition may be formulated as a free-flowing solid such as a powder or granule using a granulating agent. A preferred granulating agent useful in rendering the composition a free-flowing solid is microcrystalline cellulose. Another preferred granulating agent is fumed silicon dioxide available from commercial sources (e.g., Cabot Corp., Tuscola, Ill.) and useful in controlling granule density. Furthermore, in one embodiment, the composition as a free-flowing solid is delivered to an acidic beverage where it is dispersed into solution. To assist in dispersion of the composition into solution, the composition may include a dispersing agent. A preferred dispersing agent useful for smooth dispersal of the composition in solution is carboxymethyl cellulose. In another embodiment, the excipient is soluble coffee (also known as instant coffee). In yet another embodiment, the excipient is a nondairy creamer.

In general, an excipient is present in the composition in an amount ranging from about 5% to about 30% by weight of the total composition. In a preferred embodiment, the acid-neutralizing composition includes microcrystalline cellulose in an amount from about 2% to about 10% by weight of the total composition, carboxymethyl cellulose sodium in an amount from about 2% to about 20% by weight of the total composition, and instant coffee in an amount from about 0.1% to about 0.5% by weight of the total composition. Instant coffee is suitably added to the composition to provide an appealing coffee color. Instant coffee is not required for the composition's efficacy in reducing acidity.

The acid-neutralizing composition may also be formulated as a liquid solution. When the composition is formulated as a liquid, the excipient may be water including sterile and/or distilled water.

As described above, the acid-neutralizing composition includes alkaline substances (i.e., preferably calcium carbonate, magnesium carbonate, potassium hydroxide, magnesium hydroxide, and gelatin) that are active in reducing the acidity of an acidic food or beverage; other ingredients (i.e., vitamin D) that offer additional health and nutritional benefits; and inert ingredients (i.e., potassium chloride, bacteria and/or fungi retarders, and excipients) that provide practical effectiveness relating to composition stability and formulation. All of these ingredients are Generally Regarded As Safe (GRAS) for use by the Food and Drug Administration.

Representative acid-neutralizing compositions of the present invention are described in Examples 1–3. Example 3 describes a representative acid-neutralizing composition of this invention that includes gelatin.

The acid-neutralizing composition of the present invention may be formulated in a variety of ways. As noted above, the composition may be formulated as a free-flowing solid, such as a powder or granule. The composition of the present invention may be granulated in any one of many granulation techniques known in the art. One suitable method involves the mixing of all dry components of the composition in water to form partially agglomerated clumps, followed by drying, chopping, and shifting to produce the desired granules. Other granulation methods well known to those of ordinary skill in the art include: spray drying; extrusion and chopping; grinding; the use of a fluid bed; and high shear granulation. The formulation of an acid-neutralizing composition of this invention as a free-flowing granule is described in Example 1. In addition to flowing solids, the composition may also be formulated as a pill, tablet, or capsule. The composition may also be formulated as a liquid, such as an aqueous solution, slurry, emulsion, or syrup.

The present invention also provides coffee products. In one embodiment, this invention provides a coffee product comprising whole coffee beans and an acid-neutralizing composition. In another embodiment, a coffee product comprising ground coffee beans and an acid-neutralizing composition is provided. In these coffee products, the acid-neutralizing composition is present in an amount sufficient to produce a brewed coffee having a pH of from about pH 5.7 to about 6.1. Typically, about 10 to 20 grams of the acid-neutralizing composition added to one kilogram of coffee is sufficient to produce a brewed coffee having such reduced acidity.

As noted above, one aspect of the present invention provides methods for reducing the acidity of an acidic food or beverage by the addition of an acid-neutralizing composition. In the context of this invention, acidic foods include liquid foods, such as tomato products including tomato paste, vinegar-containing products such as salad dressing, and cranberry products including cranberry sauce. Acidic beverages include any beverage having a pH less than about 4, including coffee beverages, tea beverages, and fruit juice beverages such as tomato juice and cranberry juice beverages, and citrus fruit beverages including orange and grapefruit juice beverages.

While the pH of coffee beverages will depend on many factors, including the type of coffee bean, strength of the brew, and brewing conditions, the pH of most coffees falls within the range of from pH 4.8 to about pH 5.7. The present invention provides methods for reducing the acidity (i.e., increasing the pH) of coffee beverages. Preferably, the methods of the invention provide a coffee beverage having a pH in the range from about pH 5.7 to about pH 6.1.

Generally, the present invention provides a method of brewing coffee having reduced acidity that includes adding an acid-neutralizing composition to a coffee product in an amount sufficient to produce a brewed coffee having a pH of from about pH 5.7 to about pH 6.1. In the context of the present invention, a coffee product includes whole coffee beans, ground coffee beans, and brewed coffee.

Other known processes for the deacidification of coffee include alkaline treatment of either green or semiroasted beans at elevated temperature (e.g., 375° to 425° F.) for prolonged periods of time (e.g., 10 to 25 minutes depending upon the type of bean, its moisture content, and the roast desired). Typically, under these conditions, the deacidification is accompanied by saponification of coffee oils resulting in alteration of the coffee's flavor and aroma. To a large extent, the oils of the coffee impart its flavor and aroma.

In contrast, as described below, the methods of the present invention utilize an acid-neutralizing composition under conditions that preserve the flavor and aroma of the coffee. In the present methods, a coffee product is combined with the acid-neutralizing composition at relatively low temperature (e.g., about 220° F., the boiling point of water) for a short period of time (e.g., about 3 to 5 minutes, the time required to prepare a brewed coffee). Accordingly, the methods of this invention result in a coffee having reduced acidity without compromising the flavor, aroma, and taste integrity of the resulting brewed coffee.

In one embodiment, the present invention provides a method of brewing coffee having reduced acidity. In the method, an acid-neutralizing composition, as described above, is added to whole coffee beans to provide a whole coffee bean and acid-neutralizing composition mixture. The whole coffee bean and acid-neutralizing composition mixture is then subjected to grinding to provide a ground coffee bean and acid-neutralizing composition mixture. Finally, the ground coffee bean and an acid-neutralizing composition mixture are brewed with water to provide a brewed coffee having reduced acidity.

In this method, the reduction of acidity of a coffee beverage depends upon the quantity of the acid-neutralizing composition added to the whole coffee beans. In addition, the amount of an acid-neutralizing composition added to the whole beans will depend upon many factors including the nature and type of coffee bean. Generally, to provide a coffee beverage having reduced acidity and a pH in the range from about 5.7 to about 6.1, approximately 15 grams of the acid-neutralizing composition of this invention are added to approximately one kilogram of whole coffee beans.

In another embodiment, the present invention provides a method of brewing coffee having reduced acidity where an acid-neutralizing composition is added to ground coffee beans. In this method, the addition of an acid-neutralizing composition to ground coffee beans provides a ground coffee bean and acid-neutralizing composition mixture, which is then brewed with water to provide a brewed coffee having reduced acidity.

Similar to the above method, the reduction of acidity of a coffee beverage depends upon the quantity of the acid-neutralizing composition added to the ground coffee beans, which in turn depends upon factors including the nature and type of coffee bean. Generally, to provide a coffee beverage having reduced acidity and a pH in the range from about 5.7 to about 6.1, approximately 15 grams of the acid-neutralizing composition of this invention are added to approximately one kilogram of ground coffee beans.

In yet another embodiment, this invention provides a method of preparing a coffee beverage having reduced acidity where an acid-neutralizing composition is added directly to a brewed coffee beverage. In this method, an acid-neutralizing composition is added directly to a brewed coffee, such as a cup or pot of coffee, such that the pH of the resulting brewed coffee has a pH in the range from about pH 5.7 to about pH 6.1. As noted above, the quantity of acid-neutralizing composition to effect the reduction of acidity to this prefeffed pH range will depend upon the acidity of a brewed coffee beverage. In general, about 100 mg of acid-neutralizing composition will increase the pH of an 8-ounce cup of coffee from about pH 5 to about pH 6. Accordingly, approximately 1.2 grams of the composition would similarly reduce the acidity of a twelve-cup pot of coffee to a pH range of about pH 5 to about pH 6.

All of the methods noted above offer the advantage that the coffee brewer may reduce the acidity of her coffee beverage to suit her own taste. Accordingly, the coffee brewer may add more or less of the acid-neutralizing composition as desired.

In still another embodiment, a method for brewing coffee having reduced acidity is provided where a coffee filter impregnated with an acid-neutralizing composition is utilized in brewing the coffee beverage. In this method, ground coffee beans are placed in a coffee filter impregnated with an acid-neutralizing composition, and the coffee is then brewed in the usual manner. The acid-neutralizing composition is present in the filter in an amount sufficient to produce a brewed coffee having a pH from about pH 5.7 to about 6.1.

The methods and compositions of the present invention provide brewed coffee having reduced acidity while at the same time maintaining the taste integrity of the coffee. Taste tests have been conducted and have demonstrated that no detrimental effect to coffee flavor occurs in the practice of the methods of the present invention. In fact, in several instances, coffees produced by these methods were rated as having a better taste than plain coffee. Some taste tests and their results are described in Example 4.

As noted above, in another aspect, the invention also relates to compositions and methods useful in neutralizing excess stomach acid in humans. Like the acid-neutralizing composition noted above, the antacid composition also includes alkaline substances that afford both rapid and long-lasting antacid activity. The antacid composition includes an alkaline earth metal carbonate, preferably calcium carbonate; an alkali metal hydroxide, preferably potassium hydroxide; and an alkaline earth metal hydroxide, preferably magnesium hydroxide. In preferred embodiments, calcium carbonate is present in the composition in an amount ranging from about 20 to 90% by weight of the total composition; potassium hydroxide is present in the composition in an amount ranging from about 0.5 to about 10% by weight of the total composition; and magnesium hydroxide is present in the composition in an amount ranging from about 0.1 to about 10% by weight of the total composition.

In a more preferred embodiment, calcium carbonate is present in the composition in an amount ranging from about 25 to about 45% by weight of the total composition; potassium hydroxide is present in the composition in an amount ranging from about 1 to about 10% by weight of the total composition; and magnesium hydroxide is present in the composition in an amount ranging from about 1 to about 5% by weight of the total composition.

Of these ingredients, potassium hydroxide is the strongest and most rapid acting acid neutralizer. Magnesium hydroxide is intermediate in its neutralizing activity and supplements the antacid activity of potassium hydroxide, and calcium carbonate acts as a weak acid neutralizer and imparts long-lasting antacid activity to the composition.

In addition to the alkaline substances noted above, the antacid composition of this invention may include other ingredients. Thus, in another embodiment, the antacid composition includes potassium chloride as mouthfeel and taste enhancer. Preferably, potassium chloride is present in the composition in an amount ranging from about 0.2 to 2% by weight of the total composition.

The antacid composition of this invention may also include one or more excipients. Suitable excipients include those that enable the effective delivery of the alkaline substances and other ingredients present in the composition and include granulating and tableting agents. The granulating and tableting agents are also useful in processing the solid ingredients of the composition and formulating the antacid composition as a powder, granule, or tablet, which will dissolve or "explode" when introduced to liquid. Suitable excipients include microcrystalline cellulose, silicon dioxide, and croscarmellose sodium NF (also known as carboxy methyl cellulose-sodium or CMC sodium).

In general, one or more excipients are present in the composition in an amount ranging from about 10 to about 30% by weight of the total composition. In a preferred embodiment, the antacid composition includes croscarmellose sodium NF in an amount from about 2% to about 5% by weight of the total composition, microcrystalline cellulose in an amount from about 15% to about 25% by weight of the total composition, and silicon dioxide in an amount from about 0.1% to about 2% by weight of the total composition.

The antacid composition of the invention may also include one or more flavoring agents. Suitable flavoring agents include sweetening agents and other flavorants. Suitable sweetening agents include sugars such as monosaccharides, disaccharides, and polysaccharides, for example, glucose, fructose, dextrose and sucrose; and artificial sweeteners such as saccharine, cyclamate, and dipeptide-based sweeteners such as NutraSweet®. Suitable other flavorants include mint-containing flavorants such as spearmint and peppermint flavorants as well as other similar flavorings. The amount of flavoring agent present in the antacid composition is primarily a matter of taste preference and may vary with the flavoring agent selected and with the other ingredients in the composition. The flavoring agent may be present in an amount ranging from about 2% to about 60% and preferably from about 35% to about 45% by weight of the total composition. In a preferred embodiment, the antacid composition includes a natural spearmint flavorant and sucrose.

The preferred antacid composition of this invention is an extremely low sodium-containing composition. Besides sodium impurities present in the composition's ingredients, the only source of sodium is carboxymethyl cellulose sodium, which is present in the composition in an amount from about 2% to about 5% by weight of the total composition. Under FDA standards, such a composition is considered to be sodium free. This equates to less than 0.5 mg per serving.

Used in the amounts indicated, all of the ingredients of the antacid compositions of this invention are considered by the FDA to be generally regarded as safe (GRAS). For example, the standard manufacturing practice limit for potassium hydroxide is 1200 mg/serving. When the antacid composition of this invention is used as directed, the amount of potassium hydroxide administered is significantly less than the upper limits noted above.

Representative antacid compositions of the present invention are described in Example 5. Example 6 describes the acid-neutralizing effectiveness of some representative antacid compositions of the invention and their effectiveness in acid neutralization is compared to some commercially available antacids in Examples 7 and 8.

The antacid compositions of the invention are fast acting acid neutralizers. Their rapid rate of acid neutralization was the greatest of the antacids compared (see Example 7 and FIG. 1) and may be attributed to the presence of potassium hydroxide in the composition.

Furthermore, the antacid compositions of the invention are potent acid-neutralizing compositions. On a weight basis, the amount of antacid necessary to raise the pH of an acidic solution from pH 3.0 to pH 6.0 is substantially less for the antacids of the invention than for several commercially available antacids (see Example 8 and FIG. 2).

In addition to providing antacid compositions, the present invention also provides a method for neutralizing excess stomach acid in a human. The method comprises orally administering to the human a safe and effective amount of an antacid composition as described above. As used herein, the term "safe and effective amount" refers to a quantity of the antacid composition sufficient to provide the desired antacid effect without undue adverse side effects such as toxicity, irritation, or allergic response. The specific safe and effective amount will vary with such factors as the specific condition that is being treated, the severity of the condition, the duration of the treatment, the physical condition of the subject, the nature of any concurrent therapy, and the specific formulation and optional components utilized. However, a human patient in need of such treatment will typically receive from about 200 mg to about 2,000 mg of the antacid composition daily.

The following examples further demonstrate and describe embodiments of the present invention. The examples are given solely for the purpose of illustration and not limitation.

EXAMPLES

Example 1

In this example, a representative acid-neutralizing composition of the present invention is described. A method for combining the ingredients and formulating the composition as a free-flowing granule is also described.

| Ingredient | Percent by Weight |
|---|---|
| Calcium carbonate | 66.82 |
| Potassium hydroxide | 7.25 |
| Magnesium hydroxide | 0.67 |
| Potassium chloride | 2.67 |
| Excipient | |
| Microcrystalline cellulose (Tabulose ™, Blenver Co., Brazil) | 5.33 |
| Caboxymethyl cellulose sodium (Solutab ™, Blenver Co., Brazil) | 16.75 |
| Vitamin D (dry stabilized vitamin $D_3$-water dispersible, Vitamins, Inc., Chicago, IL) | 0.17 |
| Instant coffee (Yuban ™) | 0.35 |

A granulated formulation having the above composition was prepared as described below. To a 20-quart mixing bowl was added 3675 grams calcium carbonate, 37 grams magnesium hydroxide, 147 grams potassium chloride, 293 grams Tabulose™, 921 grams Solutab™, and 9 grams vitamin $D_3$-water dispersible. The contents of the mixing bowl were mixed for approximately 5 minutes. While mixing, a solution of 399 grams potassium hydroxide in about 400 mL of deionized water was delivered over a period of about 2 minutes to the mixed solids in the mixing bowl by way of a peristaltic pump. Upon the completion of the addition of the potassium hydroxide solution, the blend was mixed for an additional ten minutes. A solution of 19 grams instant coffee (Yuban™) in 1200 mL deionized water (prepared from the addition of 1200 mL hot deionized water to 19 grams instant coffee) was then delivered over a period of about 4.5 minutes to the mixed solids in the mixing bowl by way of a peristaltic pump. Upon the completion of the addition of the instant coffee solution, the blend was mixed for an additional five minutes. At this point, 100 to 200 mL additional water may be added to the blend, if necessary, to provide a mixture having a granular (i.e., nonpowdery) appearance. The moist formula was then mixed for approximately 20 minutes with occasional wiping of the sides of the mixing bowl with a spatula to assure a thorough mixing of the entire formula. After thorough mixing, the moist formula was transferred into a large plastic bin. The contents of the bin were then added in portions to fill the funnel of a cutting machine. The cutting machine and the auger were then powered on and the formula was granulated. After granulation, the cutting machine and auger were powered off and the granulated formula was collected using a vacuum. The granulated formula was then distributed to oven trays (approximately one pound of formula per tray), the trays were placed in an oven, and the formula dried for 30 minutes at a temperature of 180° F. The trays of formula were then rotated in the oven to assure uniform heat treatment, and dried for an additional 30 minutes. Removal from the oven and cooling provided a representative composition of the present invention formulated as a free-flowing granule.

Example 2

In this example, another representative acid-neutralizing composition of the present invention is described.

| Ingredient | Percent by Weight |
|---|---|
| Calcium carbonate | 63.33 |
| Potassium hydroxide | 11.64 |
| Magnesium hydroxide | 6.14 |
| Potassium chloride | 2.33 |
| Excipient | |
| Microcrystalline cellulose (Tabulose ™, Blenver Co., Brazil) | 6.19 |
| Carboxymethyl cellulose sodium (Solutab ™, Blenver Co., Brazil) | 8.91 |
| Vitamin D (dry stabilized vitamin $D_3$-water dispersible, Vitamins, Inc., Chicago, IL) | 0.47 |
| Magnesium stearate | 1.01 |

These ingredients were combined to provide a composition that is a free-flowing granule by the method described above in Example 1.

Example 3

In this example, a representative acid-neutralizing composition of the present invention including gelatin and bacteria and fungi retarder is described.

| Ingredient | Percent by Weight |
|---|---|
| Calcium carbonate | 62.10 |
| Potassium hydroxide | 11.42 |
| Magnesium hydroxide | 6.02 |
| Potassium chloride | 2.28 |
| Foodgrade type B gelatin | 1.83 |
| Bacteria and fungi retarder | |
| Methyl paraben | 0.02 |
| Propyl paraben | 0.08 |
| Excipient | |
| Microcrystalline cellulose (Tabulose ™, Blenver Co., Brazil) | 6.07 |
| Carboxymethyl cellulose sodium (Solutab ™, Blenver Co., Brazil) | 8.74 |
| Vitamin D (dry stabilized vitamin $D_3$-water dispersible, Vitamins, Inc., Chicago, IL) | 0.46 |
| Magnesium stearate | 1.00 |

These ingredients were combined to provide a composition that is a free-flowing granule by the method described above in Example 1.

Example 4

In this example, tests evaluating the taste of coffees prepared by the methods of the present invention are described. In these tests, the taste of coffees containing embodiments of the acid-neutralizing compositions of this invention was evaluated by coffee tasters and compared with the taste of plain coffee (i.e., the same coffee containing no acid-neutralizing composition).

In the tests, the coffee tasters rated each of nine categories on a scale from 1 (worst) to 5 (best). The categories evaluated were aroma, appearance, acidic taste, chemical taste, salt taste, sweetness, bitterness, aftertaste, and overall impression.

The following acid-neutralizing composition formulations were tested:

Formulation A:
   567 grams calcium carbonate
   28.4 grams FMA-11™ (a mixture consisting of 41.5 weight percent aluminum hydroxide, 8.0 weight percent magnesium hydroxide, 50.5 weight percent calcium carbonate; Reheis Corp., Berkeley Heights, N.J.)
   6 grams potassium chloride
   6 grams gelatin Formulation B:
   143.5 grams calcium carbonate
   3.5 grams FMA-1™
   1.8 grams aluminum hydroxide
   1.5 grams potassium chloride Formulation C:
   143.5 grams calcium carbonate
   3.5 grams FMA-11™
   1.8 grams magnesium carbonate
   1.5 grams potassium chloride Formulation D:
   140.3 grams calcium carbonate
   7.1 grams FMA-11™
   3 grams potassium chloride Formulation E:
   138.8 grams calcium carbonate
   7.1 grams FMA-11™
   4.5 grams potassium chloride Formulation F:
   137.3 grams calcium carbonate
   7.1 grams FMA-11™
   6 grams potassium chloride Each of the test coffee samples was prepared by the addition of 1.4 grams of one of the above formulations to a 12-cup pot of brewed coffee Millstone Breakfast Blend™.

The taste test results are summarized in the following table. Average score refers to the average overall taste on a scale from 1 (worst) to 5 (best).

| Formulation | Average score |
|---|---|
| Plain coffee | 3.8 (2.75) |
| A | 3.8 (2.34) |
| B | 4.3 (3.00) |
| C | 3.6 (2.88) |
| D | 3.9 (2.86) |
| E | 3.4 |
| F | 3.1 |

The values represent an average of the values assigned by eight taste testers in the age group of 25 to 35 years old.

The values in parentheses represent the results of a subsequent taste test by eight taste testers in the age group of 55 to 75 years old.

As summarized in the table above, several acid-neutralizing composition formulations were found to have tastes more pleasing than plain coffee. In the taste tests, Formulation B was determined to be the most flavorful coffee.

Example 5

Representative Antacid Compositions

In this Example, representative antacid compositions of the invention (i.e., Formulations G–P) are described. Formulations G–P were prepared by combining the ingredients tabulated below in the amounts specified and formulating the resulting mixture as a free-flowing granule as described above in Example 1.

The following antacid composition formulations were prepared:

| Ingredient | Percent by Weight |
|---|---|
| Calcium carbonate | 72.0 |
| Potassium hydroxide | 5.0 |
| Magnesium hydroxide | 0.7 |
| Excipients | |
| Microcrystalline cellulose | 20.3 |
| Croscarmellose sodium NF | 2.0 |

| Ingredient | Percent by Weight |
|---|---|
| Calcium carbonate | 46.51 |
| Potassium hydroxide | 3.80 |
| Magnesium hydroxide | 4.07 |
| Excipient | |
| Croscarmellose sodium NF | 2.01 |
| Microcrystalline cellulose | 20.07 |
| Silicon dioxide | 0.50 |
| Flavoring agents | |
| Natural spearmint flavor | 2.71 |
| Fructose | 20.34 |

| Ingredient | Percent by Weight |
|---|---|
| Calcium carbonate | 45.28 |
| Potassium hydroxide | 3.70 |
| Magnesium hydroxide | 3.96 |
| Excipient | |
| Croscarmellose sodium NF | 1.95 |
| Microcrystalline cellulose | 19.54 |
| Silicon dioxide | 0.48 |
| Flavoring agents | |
| Natural spearmint flavor | 5.28 |
| Fructose | 19.80 |

Formulation J:

| Ingredient | Percent by Weight |
|---|---|
| Calcium carbonate | 45.74 |
| Potassium hydroxide | 3.73 |
| Magnesium hydroxide | 4.00 |
| Excipient | |
| Croscarmellose sodium NF | 2.03 |
| Microcrystalline cellulose | 20.00 |
| Silicon dioxide | 0.50 |
| Flavoring agents | |
| Natural spearmint flavor | 5.33 |
| Sucrose | 18.67 |

Formulation K:

| Ingredient | Percent by Weight |
|---|---|
| Calcium carbonate | 41.44 |
| Potassium hydroxide | 3.38 |
| Magnesium hydroxide | 3.62 |
| Excipient | |
| Croscarmellose sodium NF | 2.05 |
| Microcrystalline cellulose | 20.05 |
| Silicon dioxide | 0.45 |
| Flavoring agents | |
| Natural spearmint flavor | 4.83 |
| Sucrose | 24.16 |

Formulation L:

| Ingredient | Percent by Weight |
|---|---|
| Calcium carbonate | 31.55 |
| Potassium hydroxide | 1.61 |
| Magnesium hydroxide | 2.68 |
| Excipient | |
| Croscarmellose sodium NF | 2.05 |
| Microcrystalline cellulose | 20.54 |
| Silicon dioxide | 0.50 |
| Flavoring agents | |
| Natural spearmint flavor | 5.36 |
| Sucrose | 35.71 |

Formulation M:

| Ingredient | Percent by Weight |
|---|---|
| Calcium carbonate | 28.19 |
| Potassium hydroxide | 1.44 |
| Magnesium hydroxide | 2.39 |
| Excipient | |
| Croscarmellose sodium NF | 2.00 |
| Microcrystalline cellulose | 20.00 |
| Silicon dioxide | 0.51 |
| Flavoring agents | |
| Natural spearmint flavor | 5.58 |
| Sucrose | 39.88 |

Formulation N:

| Ingredient | Percent by Weight |
|---|---|
| Calcium carbonate | 28.57 |
| Potassium hydroxide | 1.60 |
| Magnesium hydroxide | 1.50 |
| Excipient | |
| Croscarmellose sodium NF | 5.51 |
| Microcrystalline cellulose | 20.00 |
| Silicon dioxide | 0.50 |

-continued

Formulation N:

| Ingredient | Percent by Weight |
|---|---|
| Flavoring agents | |
| Natural spearmint flavor | 7.71 |
| Sucrose | 34.60 |

Formulation O:

| Ingredient | Percent by Weight |
|---|---|
| Calcium carbonate | 29.40 |
| Potassium hydroxide | 1.60 |
| Magnesium hydroxide | 1.50 |
| Excipient | |
| Croscarmellose sodium NF | 4.00 |
| Microcrystalline cellulose | 20.00 |
| Silicon dioxide | 0.50 |
| Flavoring agents | |
| Natural spearmint flavor | 8.5 |
| Sucrose | 34.50 |

Example 6

Acid-Neutralizing Effectiveness of Representative Antacid Compositions

This Example describes the acid-neutralizing effectiveness of representative antacid compositions (i.e., Formulations G–N) prepared as described in Example 5 above. In each neutralization experiment, 300 mg of an antacid tablet was crushed into a powder and added to a 100 gram solution of aqueous hydrochloric acid having a pH of about 1.8. The pH of the continuously stirred solution was measured prior to the addition of the antacid and then every minute for ten minutes after the antacid addition.

The pH values of the solutions as a function of time are presented in the table low.

| Antacid Effectiveness: Change in pH over time Formulation | | | | | | | | |
|---|---|---|---|---|---|---|---|---|
| Time (min.) | G | H | I | J | K | L | M | N |
| 0 | 1.57 | 1.73 | 1.75 | 1.38 | 1.25 | 1.93 | 1.95 | 1.95 |
| 1 | 6.45 | 8.28 | 8.64 | 9.23 | 9.14 | 8.76 | 7.73 | 8.05 |
| 2 | 7.66 | 9.13 | 9.47 | 9.51 | 9.55 | 9.26 | 8.84 | 8.95 |
| 3 | 8.73 | 9.59 | 9.89 | 9.59 | 9.68 | 9.63 | 9.20 | 9.31 |
| 4 | 9.11 | 9.86 | 10.16 | 9.63 | 9.74 | 9.80 | 9.40 | 9.57 |
| 5 | 9.3 | 10.07 | 10.34 | 9.66 | 9.78 | 9.89 | 9.56 | 9.77 |
| 6 | 9.48 | 10.23 | 10.52 | 9.69 | 9.80 | 9.96 | 9.66 | 9.91 |
| 7 | 9.54 | 10.36 | 10.59 | 9.73 | 9.87 | 10.06 | 9.79 | 10.05 |
| 8 | 9.61 | 10.45 | 10.68 | 9.75 | 9.89 | 10.14 | 9.88 | 10.18 |
| 9 | 9.66 | 10.54 | 10.74 | 9.79 | 9.92 | 10.24 | 9.97 | 10.27 |
| 10 | 9.73 | 10.61 | 10.8 | 9.81 | 9.95 | 10.35 | 10.04 | 10.35 |

The results show that when added to an acidic solution the representative antacid compositions of the invention rapidly achieve a high level of acid neutralization (i.e., pH 8–9 after 1 to 2 minutes). Final pH values of about 10 are attained for the treated solutions shortly thereafter.

Example 7

Comparison of Antacid Effectiveness of Invention Relative to Commercial Antacids The acid-neutralizing effectiveness for a representative antacid composition of the invention (Formulation N from Example 6) was compared to several commercially available, over-the-counter antacid compositions. The commercially available antacids used in the comparison included:

| Antacid | Active Ingredients |
|---|---|
| MYLANTA (Johnson & Johnson/Merck, Fort Washington, PA) | Calcium carbonate, magnesium hydroxide |
| GAVISCON (Smith Kline Beecham, Pittsburgh, PA) | Aluminum hydroxide, sodium bicarbonate |
| TUMS E-X (Smith Kline Beecham, Pittsburgh, PA) | Calcium carbonate |
| MAALOX (Rhone-Poulenc Rover Pharmaceuticals Inc. Collegeville, PA) | Aluminum hydroxide, magnesium hydroxide |
| ROLAIDS (Warner-Lambert Co., Morris Plains, NJ) | Calcium carbonate, magnesium hydroxide |
| MEDACID (Bristol-Meyers Squibb Co., New York, NY) | Calcium carbonate, magnesium carbonate, magnesium oxide |
| PRELIEF (AkPharma Inc., El Paso, TX) | Calcium glycerin phosphate |

In these comparative experiments, 300 mg of each antacid was crushed and added to 100 g of an aqueous hydrochloric acid solution (0.015 M HCl, pH 1.80) with stirring. The pH of the continuously stirred solution was monitored over time (i.e., pH measured prior to addition of antacid and then every minute for ten minutes after antacid addition) to determine the rate of acid neutralization as well as the extent to which each antacid neutralized the acidic solution (i.e., the final pH of the solution). The results of acid-neutralizing experiments comparing a representative antacid composition of this invention (i.e., Formulation N) to the commercially available antacids MYLANTA, GAVISCON, TUMS E-X, MAALOX, ROLAIDS, MEDACID, and PRELIEF are graphically illustrated in FIG. 1.

The representative antacid composition of the present invention is the fastest acting of the antacids compared. Referring to FIG. 1, the results show that after one minute, the representative antacid composition of the invention reduced the acidity of the aqueous solution and elevated its pH to about 9. For the commercial antacids, after one minute, PRELIEF raised the pH of the solution to about 7.5, MEDACID, ROLAIDS, TUMS, and MYLANTA raised the pH of the solution to between about 4 to 5, while MAALOX and GAVISCON showed little effect of the solution's pH. The rapid rate of acid neutralization exhibited by the antacid of the invention is the greatest of the antacids compared.

Referring to FIG. 1, at the four-minute time point, only MEDACID had neutralized the acidic solution to the same extent as the representative antacid composition of this invention (i.e., pH about 10). Solutions containing PRELIEF, ROLAIDS, TUMS, and MYLANTA had pH values between about 5 to 7, and the acidity of solutions treated with MAALOX and GAVISCON remain essentially unchanged (i.e., pH about 2 to 3). After ten minutes, acid neutralization appeared nearly complete. The antacid composition of the invention provides a solution having a final pH of about 10.5, MEDACID about pH 10.5, ROLAIDS about pH 10, MYLANTA about pH 8.5, PRELIEF about pH 7.5, TUMS about pH 7, MAALOX about pH 3, and GAVISCON about pH 2.5.

Referring to FIG. 1, it appears that generally the rapid acid-neutralizing action of the antacid compositions may be attributed their rapid acting components: potassium hydroxide and magnesium hydroxide for the antacid of this invention; magnesium oxide for MEDACID; magnesium hydroxide for ROLAIDS and MYLANTA; and calcium glycerol phosphate for PRELIEF. Referring to FIG. 1, the secondary neutralizing effect exhibited by the antacid compositions of the present invention, and MEDACID, ROLAIDS, and MYLANTA may be attributed to calcium carbonate, their long-lasting antacid component. The acid neutralization curves for TUMS and PRELIEF reflect their having a single acid-neutralizing ingredient. The aluminum hydroxide containing antacids, GAVISCON and MAALOX, appear to be the least effective in neutralizing acid of all the antacids compared.

Example 8

Comparison of Antacid Effectiveness of the Invention and Commercial Antacids on a Weight Basis In a comparative experiment, powdered antacids were added to 150 grams of an aqueous solution of hydrochloric acid (pH 3.0) with stirring. For each solution, powdered antacid was added until the pH of the solution was raised to pH 6.0. In the experiment, each portion of added antacid was allowed to dissolve and establish the pH before the next portion was added.

Figure 2:
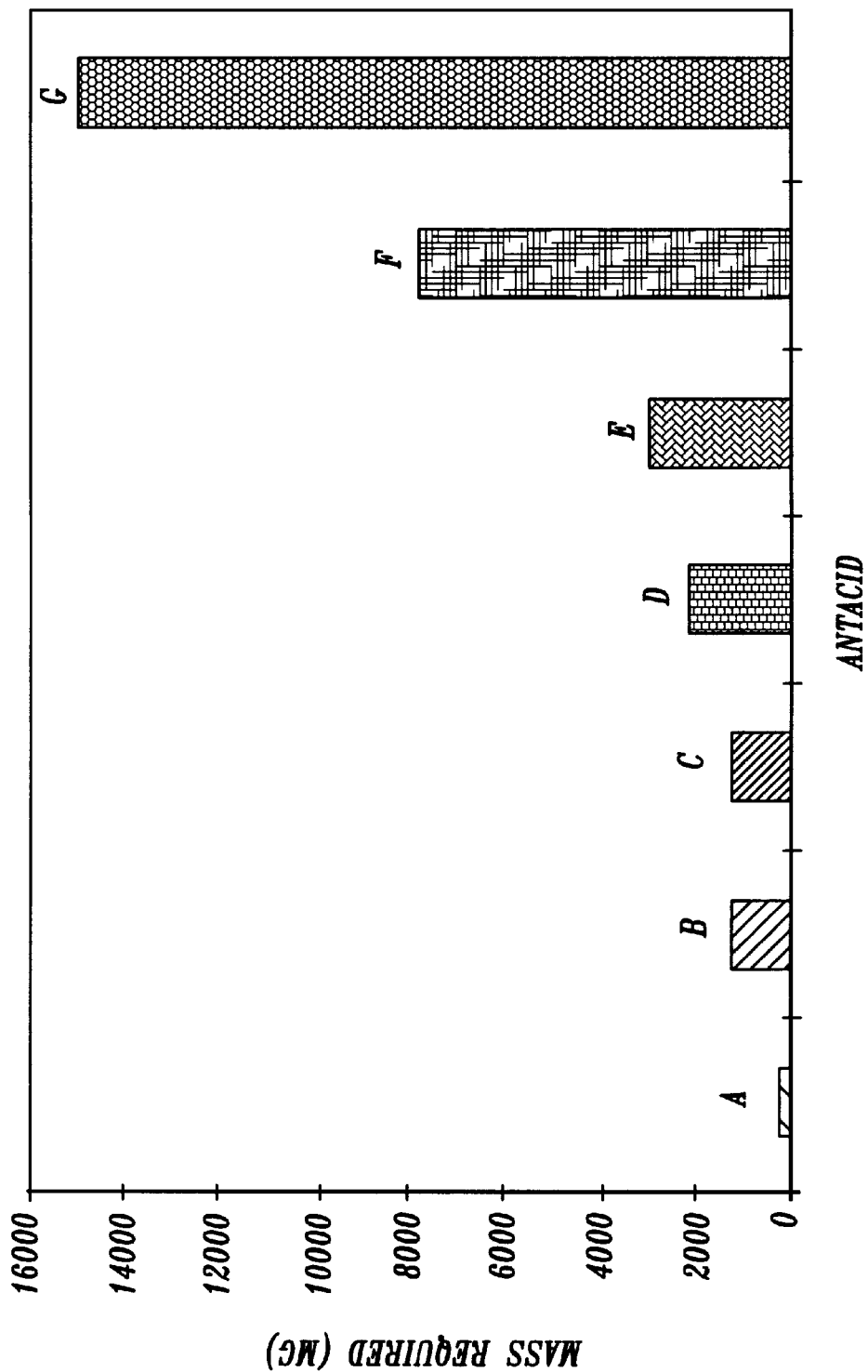
FIG. 2 is a bar graph comparing the weight effectiveness in adjusting the pH of a solution from pH 3.0 to pH 6.0 with a representative antacid composition of the present invention (a) and several commercially available antacids: ROLAIDS (b), MYLANTA (c), TUMS (d), MAALOX (e), CVS (f), and GAVISCON (g).

The results, summarized below and graphically illustrated in FIG. 2, demonstrate that the representative antacid composition of the present invention (Formulation N from Example 6) is more potent than the commercially available antacids compared on a weight basis. The representative antacid, Formulation N, was about 5 times more potent than ROLAIDS, nearly 10 times more potent than TUMS, and more than 50 times more potent than GAVISCON. It is also noted that the deacidifier composition of Example I may be used as an antacid, and when subjected to the comparative testing of the present example, only 195 mg is required for the desired neutralizing effect.

| Antacid | Antacid Potency by Weight | |
| --- | --- | --- |
| | Amount Antacid Added (mg) | Relative Potency |
| Formulation N | 245 | 1.00 |
| ROLAIDS | 1,271 | 0.19 |
| MYLANTA | 1,372 | 0.18 |
| TUMS | 2,190 | 0.11 |
| MAALOX | 3,007 | 0.08 |
| CVS | 6,427 | 0.04 |
| GAVISCON | 15,000 | 0.02 |

In summary, the antacid compositions of this invention are the most rapid acting and provide the greatest acid neutralization of all the commercial antacids compared.

While the preferred embodiment of the invention has been illustrated and described, it will be apparent that various changes can be made therein without departing from the spirit and scope of the invention.

The embodiments of the invention in which an exclusive property or privilege is claimed are defined as follow:

1. A method for neutralizing excess stomach acid in a human, comprising orally administering to the human in need thereof, a safe and effective amount of an antacid composition, wherein the antacid composition comprises calcium carbonate present in the composition in an amount ranging from 20 to 75 percent by weight of the total composition potassium hydroxide present in an amount ranging from 0.5 to 10 percent by weight of the total composition and magnesium hydroxide present in an amount ranging from 0.1 to 10 percent by weight of the total composition, wherein the composition administered is compounded to at least partially dissolve in the stomach to neutralize excess stomach acids.

2. The method of claim 1, wherein the administered antacid composition comprises calcium carbonate, present in the composition in an amount ranging from 25 to 45 percent by weight of the total composition; potassium hydroxide, present in an amount ranging from 1 to 5 percent by weight of the total composition; and magnesium hydroxide, present in an amount ranging from 1 to 5 percent by weight of the total composition.

3. The method of claim 1, wherein the antacid administered comprises potassium hydroxide included at a level of from 1 to 5 percent by weight of the total composition.

4. The method of claim 2, wherein the antacid composition further comprises an excipient.

5. The method of claim 4, wherein the excipient is a granulating agent.

6. The method of claim 2, wherein the antacid composition further comprises a flavoring agent.

7. The method of claim 6, wherein the flavoring agent is a mint-containing flavorant.

8. A method for neutralizing excess stomach acid in a human, comprising orally administering to the human in need thereof, a safe and effective amount of an antacid composition, wherein the antacid composition comprises calcium carbonate present in the composition in an amount ranging from 20 to 75 percent by weight of the total composition potassium hydroxide present in an amount ranging from 0.5 to 10 percent by weight of the total composition and magnesium hydroxide present in an amount ranging from 0.1 to 10 percent by weight of the total composition, wherein the composition disperses throughout the gastric environment to neutralize excess stomach acids.

\* \* \* \* \*

UNITED STATES PATENT AND TRADEMARK OFFICE
CERTIFICATE OF CORRECTION

PATENT NO. : 6,066,342
DATED : May 23, 2000
INVENTOR(S) : I.M. Gurol et al.

Page 1 of 2

It is certified that error appears in the above-identified patent and that said Letters Patent is hereby corrected as shown below:

| COLUMN | LINE | |
|---|---|---|
| Pg. 1, col. 1 | Assignment | "Tamer" should read --TAMER-- |
| Pg. 1, col. 2 | Attorney, Agent, or Firm | "pllc" should read --PLLC-- |
| 22 | 9 | "follow:" should read --follows:-- |
| 22 (Claim 1, | 18 line 7) | "composition potassium" should read --composition, potassium-- |
| 22 (Claim 1, | 20 line 9) | "composition and" should read --composition, and-- |
| 22 (Claim 8, | 53 line 7) | "composition potassium" should read --composition, potassium-- |

UNITED STATES PATENT AND TRADEMARK OFFICE
CERTIFICATE OF CORRECTION

PATENT NO. : 6,066,342
DATED : May 23, 2000
INVENTOR(S) : I.M. Gurol et al.

Page 2 of 2

It is certified that error appears in the above-identified patent and that said Letters Patent is hereby corrected as shown below:

COLUMN     LINE

22     55     "composition and" should read --composition, and--
(Claim 8,    line 9)

Signed and Sealed this

Eighth Day of May, 2001

Attest:

NICHOLAS P. GODICI

Attesting Officer     Acting Director of the United States Patent and Trademark Office